(12) United States Patent
Leigh et al.

(10) Patent No.: US 9,482,594 B2
(45) Date of Patent: Nov. 1, 2016

(54) DIAGNOSTIC MODULE

(75) Inventors: Kevin B Leigh, Houston, TX (US);
George D Megason, Spring, TX (US)

(73) Assignee: Hewlett Packard Enterprise Development LP, Houston, TX (US)

( * ) Notice: Subject to any disclaimer, the term of this patent is extended or adjusted under 35 U.S.C. 154(b) by 200 days.

(21) Appl. No.: 14/368,354

(22) PCT Filed: Mar. 8, 2012

(86) PCT No.: PCT/US2012/028264
§ 371 (c)(1),
(2), (4) Date: Jun. 24, 2014

(87) PCT Pub. No.: WO2013/133835
PCT Pub. Date: Sep. 12, 2013

(65) Prior Publication Data
US 2015/0029495 A1    Jan. 29, 2015

(51) Int. Cl.
| | | |
|---|---|---|
| *G01M 11/00* | (2006.01) | |
| *G01N 21/94* | (2006.01) | |
| *G01N 21/88* | (2006.01) | |
| *G02B 6/38* | (2006.01) | |
| *B08B 5/02* | (2006.01) | |
| *H04Q 1/02* | (2006.01) | |

(52) U.S. Cl.
CPC ............... *G01M 11/30* (2013.01); *B08B 5/02* (2013.01); *G01N 21/88* (2013.01); *G01N 21/94* (2013.01); *G02B 6/385* (2013.01); *G02B 6/3866* (2013.01); *H04Q 1/09* (2013.01); *H04Q 1/15* (2013.01)

(58) Field of Classification Search
None
See application file for complete search history.

(56) References Cited

U.S. PATENT DOCUMENTS

| | | | |
|---|---|---|---|
| 6,765,658 B2 | 7/2004 | Nguyen et al. | |
| 7,042,562 B2 | 5/2006 | Kiani et al. | |
| 7,239,788 B2 | 7/2007 | Villeneuve | |
| 7,681,482 B1 | 3/2010 | Kubinski et al. | |
| 7,808,624 B2* | 10/2010 | Wells | G01M 11/31 356/73.1 |
| 8,988,670 B2* | 3/2015 | Zhou | B08B 5/02 356/73.1 |
| 9,151,694 B2* | 10/2015 | Wilson | B08B 1/00 |
| 2003/0221706 A1* | 12/2003 | Kiani | B08B 1/00 134/6 |
| 2004/0125366 A1 | 7/2004 | Kiani et al. | |
| 2008/0073485 A1 | 3/2008 | Jahn et al. | |
| 2008/0187278 A1 | 8/2008 | Young | |
| 2010/0295936 A1 | 11/2010 | Koreeda et al. | |
| 2010/0316334 A1 | 12/2010 | Kewitsch | |
| 2011/0085158 A1 | 4/2011 | Motter et al. | |
| 2011/0116755 A1 | 5/2011 | Rolston | |

OTHER PUBLICATIONS

Brown, M., Achieving IEC Standard Compliance for Fiber-optic Connector Quality, (Research Paper), Feb. 21, 2011, 4 Pages, Retrieved Jun. 23, 2014.
International Searching Authority, The International Search Report and the Written Opinion, Nov. 7, 2012, 9 pages for PCT/US2012/028264.

\* cited by examiner

*Primary Examiner* — Gordon J Stock, Jr.
(74) *Attorney, Agent, or Firm* — Hewlett Packard Enterprise Patent Department

(57) ABSTRACT

A diagnostic module may include an inspection device, a cleaning device, and in various other examples, a verification device. The inspection device may inspect an optical fiber end-face of an optical fiber. The cleaning device may clean the optical fiber end-face of the optical fiber. The diagnostic module may automatically move from an optical connector to another optical connector.

11 Claims, 3 Drawing Sheets

DIAGNOSTIC MODULE

BACKGROUND

A system can include multiple electronic devices. To allow communication with the electronic devices, a backplane infrastructure can be provided in the system, where the backplane infrastructure has connectors to connect with respective mating connectors of the electronic devices. The connectors of the backplane infrastructure can include optical connectors and cables to optically connect to respective electronic devices.

BRIEF DESCRIPTION OF THE DRAWINGS

Some embodiments are described with respect to the following figures.

DETAILED DESCRIPTION

Figure 1:
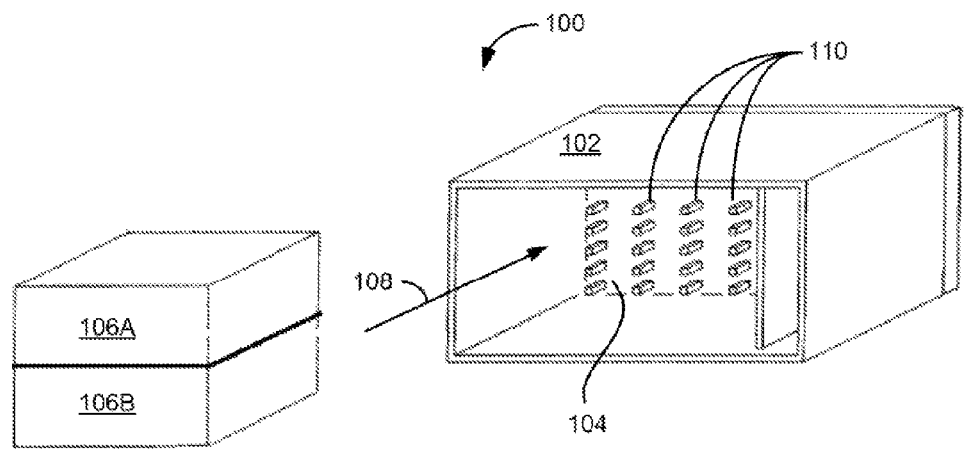
FIG. 1 illustrates a system in accordance with an example of the present disclosure.

Electronic devices, such as processing devices, storage devices, communications devices, management devices, and so forth, can be mounted in a rack (or an enclosure), which includes a frame and other support elements for holding the electronic devices. The rack provides receptacles into which the electronic devices can be inserted. The rack can also include a backplane infrastructure for connection to the electronic devices that have been inserted into the rack. When electronic devices are mounted in the rack, connectors on the electronic devices can mate with connectors of the backplane infrastructure. The connectors of the backplane infrastructure are connected to communications media (e.g. optical fibers, electrical wires, etc.) to allow for communication among the electronic devices.

A backplane infrastructure can include optical connectors for optical connection with respective optical connectors of the electronic devices. It is noted that the electronic devices and the connector infrastructure can also include electrical connectors for electrically connecting the electronic devices to the backplane infrastructure. In the ensuing discussion, reference is made to just optical connectors—note, however, that various components discussed below can also include or be utilized in conjunction with electrical connectors.

In some examples, a backplane infrastructure can include an integrated and fixed arrangement of optical connectors for connection to respective electronic devices. An integrated and fixed arrangement of optical connectors refers to an arrangement in which the optical connectors are affixed to a support structure of the backplane infrastructure such that the optical connectors have to be connected to or disconnected from all electronic devices in a system at the same time. These optical connectors may have multiple ferrules, where each ferrule organizes multiple optical fibers. Generally, a ferrule of an optical connector refers to an interface for an optical fiber, where the interface allows for optical communication between the optical fiber and another optical component. The ferrules can be fixed with the optical connector or alternatively may be removably coupled to the optical connector.

In systems utilizing optical connectors, for example optical blind-mate connectors, the optical connectors are typically cleaned before various system modules are inserted and blind-mated with respective optical connectors, especially when system modules are inserted several months after the initial infrastructure installation. This may reduce communication errors attributed to dust and debris that may accumulate on an end-face of the optical fibers. An end-face, as used herein, is a termination of an optical fiber, or the portion of the optical fiber that is to interface with another component or media. Cleaning the optical connectors and/or optical fiber end-faces of a computing system is a time consuming and error prone task given the multiple connectors which may include multiple optical fibers. Furthermore, once cleaned, verification of the multiple optical connections may be needed. Verification steps may further increase the likelihood of contamination and may result in the loss of additional time and resources to repeatedly clean the connectors and/or to manually record the cleaning process/results.

In accordance with some implementations, a diagnostic module to inspect, clean and verify multiple optical connectors is disclosed. The diagnostic module may be inserted into the rack, in a manner similar to an intended electronic device. Once inserted, the system may locate multiple optical connectors which include a plurality of ferrules organizing a plurality of optical fibers. Upon location of an optical fiber, the system may inspect and clean the optical fiber end-face. The system may be programmed to iteratively clean and inspect the optical fiber end-faces of multiple optical connectors.

Upon inspection and cleaning of the various optical fiber end faces, the diagnostic module may be further configured by an external manager via the external management link to verify various communications via the optical media. A diagnostic module may communicate with one or multiple other diagnostic modules for the verifications. In one example, a continuous (DC) signal may be transmitted across the optical fiber. In another example, a predetermined optical signal pattern may be transmitted across the optical fiber. Upon receipt of the continuous optical signal or predetermined optical signal pattern, verification of successful transmission may be obtained. The results may be obtained before and/or after inspection and cleaning. Results may be chronologically stored in the diagnostic module and/or sent to the external manager via the external link. The verification results may be utilized for various record-keeping and maintenance purposes including initial product shipment, field maintenance and warranty repairs.

FIG. 1 illustrates an example system 100 that has a rack structure 102 including a backplane 104. The backplane 104 includes a plurality of connectors 110. The connectors 110 may be optical connectors organizing multiple ferrules (not illustrated), which in turn organize multiple optical fibers (not illustrated). The connectors 110 may be configured to mate with respective connectors disposed on electronic devices configured for insertion into rack 102. In the illustrated example, a plurality of diagnostic modules 106A-B may be coupled to the rack system 102 as indicated by arrow 108. The diagnostic modules 106A-B, may couple to the backplane 103 within the rack 102 and are to automatically inspect, clean, and verify the plurality of optical connectors 110 disposed on the backplane 104 within the rack 102.

The diagnostic modules 106A-B, as will be discussed in more detail herein, may be configured to iteratively inspect, clean, and verify multiple connectors. As used herein, inspection may include inspecting an end-face of an optical fiber for dust, debris, or other imperfections. Cleaning, as used herein, may include various manners of removing dust or debris and/or repairing the end-face of the optical fiber. Verification, as used herein, may include the use of a predetermined data transmitted across the optical fiber end-face to determine one or more transmission characteristics associated with the optical fiber. While the diagnostic module 106A-B, as illustrated in FIG. 1, includes components configured to inspect, clean, and verify an end-face of an optical fiber, other diagnostic modules may include fewer components, for example, a diagnostic module may be configured to inspect and clean an end-face of an optical fiber. Other combinations of components and their functionality are contemplated.

Figure 2:
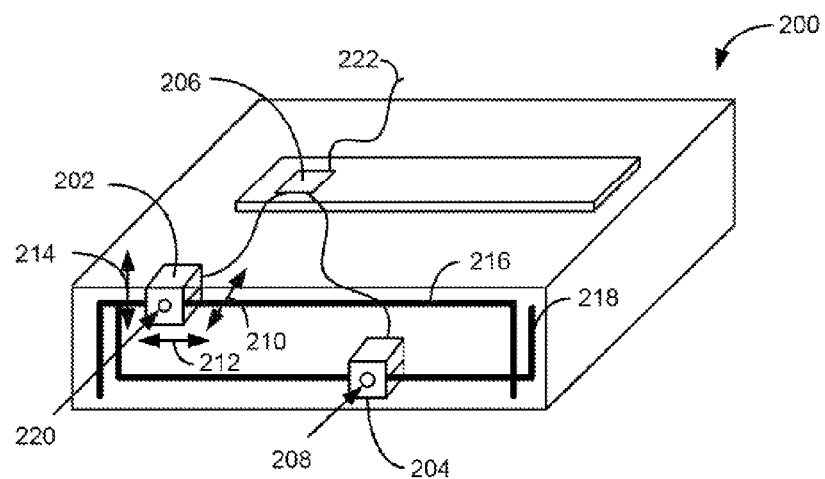
FIG. 2 is a perspective view of a diagnostic module according to some implementations.

Referring to FIG. 2, a system is illustrated in accordance with an example of the present disclosure. The system 200 may be one embodiment of a diagnostic module as illustrated in FIG. 1 (e.g. 106A-B). The system of FIG. 2 includes an inspection device 202, a cleaning device 204, and a controller 206. Other components may be included without deviating from the scope of the disclosure. The system 200 is configured for insertion into a rack (not illustrated) and may include a housing designed for integration into specific rack systems, or alternatively, may include a generic housing designed for integration into a variety of rack systems.

The inspection device 202 is to inspect an optical fiber end-face within an optical connector. The inspection device 202, in various embodiments, may be guided to an optical connector via an actuation mechanism (not shown) under the control of the controller 206. The optical connector may include indicia to facilitate identification and differentiation of one connector from others, to identify ferrule configuration, or proper seating of ferrules in the infrastructure backplane connector. In various examples, the inspection device 202 may comprise a first camera (not illustrated) to facilitate the controller in guiding the inspection device to the appropriate connector, and a second camera 220, for example a high resolution camera, to capture an image of the optical fiber end-face. The inspection device may include a light source to provide proper lighting from various angles for the camera to capture high quality images. Alternatively, the controller 206 may communicate with the controllers in other diagnostic modules to send DC optical signal via the corresponding optical fibers on the optical connector being inspected, so that the camera can capture high quality images of the dust silhouettes. The image in various examples maybe capable of distinguishing defects in the optical fiber end-face from debris such as dust, aid identifying proper seating of the ferrules in the connector. The images generated by the inspection device 202 may be stored in memory in the diagnostic module, or sent to an external manager via the external link, for later analysis or utilized for a comparison with other images to determine a window of when the damage may have occurred (e.g., during shipping). Other uses are contemplated.

The cleaning device 204 is to clean the optical fiber end-face within the optical connector. The cleaning device 204 may clean the optical fiber end-face in response to a result of the inspection, or alternatively, may clean the optical fiber end-face independent of a result of the inspection. In various examples, the cleaning device 204 may be guided to an optical connector via an actuation mechanism (not shown) under the control of the controller 206. The optical connector may again include indicia to facilitate identification and differentiation of one connector from others. The cleaning device 202 may include various cleaning mechanisms. For example, a cleaning device 202 may include a material having a cleaning solution disposed thereon, a mechanism to distribute a cleaning solution, or a compressed gas system 208 to disperse a compressed gas, for example, air to dislodge any debris or dust.

The controller 206 is coupled to the inspection device 202 and the cleaning device 204 and is configured to actuate the inspection device 202 to locate and inspect the optical fiber end-face and actuate the cleaning device 204 to locate and clean the optical fiber end-face. The controller 206 may acquire configuration information of the optical connector from an identification device on the optical connector, e.g., RFID tag. The configuration information may include number of ferrules, number of fibers on each ferrule, optical fiber type, etc. The controller 206 may be a processor configured to execute a plurality of instructions stored on a computer readable medium, may be an application specific integrated circuit (ASIC), may comprise logic configured to perform various functions, and/or other components. The controller 206 may be disposed, for example, on a printed circuit board (PCB) coupled to both the inspection device and the cleaning device. The controller 206 is coupled to an external manager via the external link 222 to receive instructions and to report results. The controller may be coupled to a storage device (not shown) in the diagnostic module to record the results chronologically, result statistics, etc. The controller 206 may activate a pass/fail indicator in the infrastructure, e.g., turn on green/red LED, after the inspection.

In various examples, the controller 206 is configured to locate the optical fibers within the optical connector. In one example, the controller may utilize a camera disposed on each of the cleaning device 204 and the inspection device 202 to guide the respective device into position. Alternatively, the controller 206 may be programmed with a location of each optical connector such that upon insertion into the rack, the controller 206 is able to transition the inspection device 202 and the cleaning device 204 into proper locations. The controller 206 may position the various devices within the system 200 in parallel or serially. In other words, the controller 206 may be configured to control the inspection device 202 to inspect a first optical connector and the cleaning device 204 to clean a second optical connector. Alternatively, the controller 206 may be configured to control a single device at a point in time.

In the illustrated example, the diagnostic module 200 includes a plurality of rails 216, 218. The rails 216, 218 may be associated with the inspection device 202 and the cleaning device 204, respectively, and facilitate positioning of the inspection device 202 and the cleaning device 204 at multiple optical connectors. The plurality of rails 216, 218 may enable horizontal movement 212, vertical movement 214, and actuation of the respective device between a retracted position and an extended position as indicated by arrow 210. Actuation between an extended position and retracted position, as indicated by arrow 210, enables the devices 202, 204 to engage the optical connectors to perform their respective functions. In one example, each device may have access to an independent rail system thereby enabling parallel control of the inspection device 202 and the cleaning device 204. In another example, a single rail system may be utilized for all devices, thereby requiring serial control of the inspection device 202 and the cleaning device 204. In yet another example, hinged robotic arms may be used to position, extend and retract the inspection device 202 and the cleaning device 204.

In various examples, the controller 206 may control an actuation mechanism, for example a servo or motor, to selectively position the inspection device 202 and the cleaning device 204. The actuation mechanism may enable the inspection device 202 and the cleaning device 204 to move along the rails in a horizontal direction 212 (an x-direction), a vertical direction 214 to (a y-direction), and between extended and retracted positions 210 (e.g., a z-direction). The actuation mechanism may include various other components including various gears, levers, etc.

Figure 3:
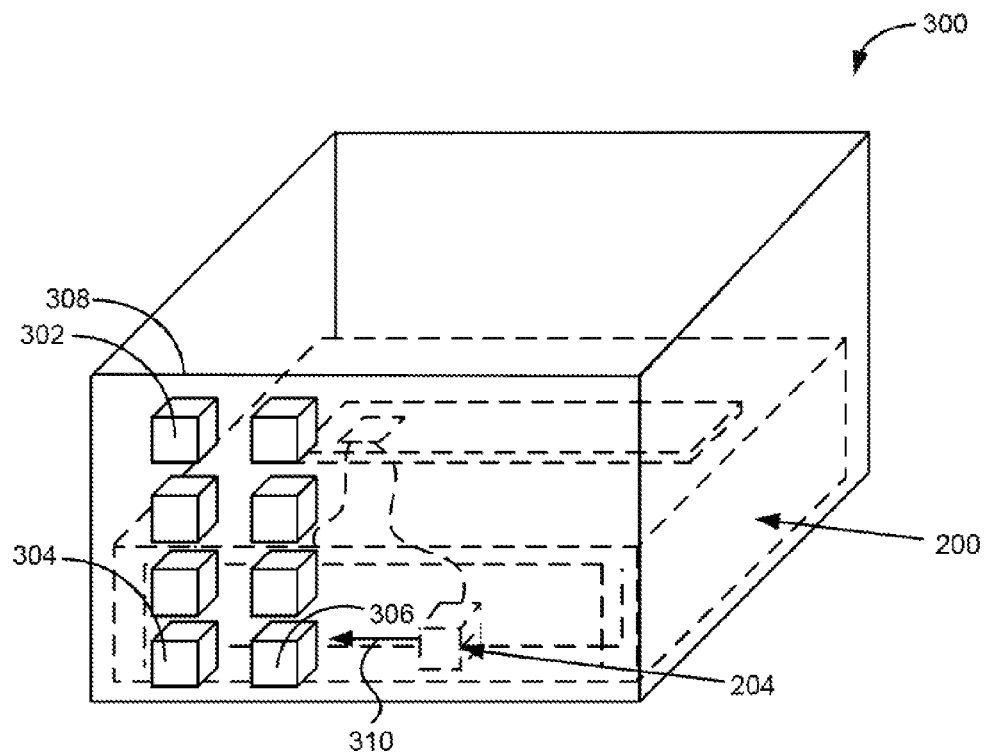
FIG. 3 is a perspective view of a diagnostic module coupled to a rack infrastructure in accordance with an example of the present disclosure.

Referring to FIG. 3, a diagnostic module 200 is illustrated in a mated condition within a rack system 300. The rack system 300 includes a backplane 308 having multiple optical connectors, three of which are labeled 302, 304, and 306. The backplane may include more optical connectors, but for the purposes of this illustration, only 8 connectors are shown. The optical connectors 302, 304, and 306 are configured to blind-mate with correspondingly disposed optical connectors on electronic devices disposed within the rack. As illustrated, a diagnostic module 200 is coupled to the rack. The diagnostic module 200 may include an inspection device and a cleaning device as discussed with reference to FIG. 2. In an initial phase, the controller may actuate the inspection device and the cleaning device into retracted positions, such that neither the inspection device nor the cleaning device interfaces with an optical connector.

Upon initiation of the diagnostic module 200, the controller may control the inspection device to locate and inspect a first optical connector 304. As illustrated, the controller has actuated the inspection device to locate and inspect a first optical connector 304. In parallel the controller may actuate the cleaning device to locate and clean a second optical connector 306. Upon actuation of the cleaning device, the cleaning device may locate the second optical connectors as illustrated by arrow 310. In the illustrated example, both the inspection device and the cleaning device are coupled to independent rail systems thereby enabling a first optical connector 304 to be inspected while a second optical connector 306 is cleaned. The controller may actuate the inspection device and the cleaning device to inspect and clean each optical fiber end-face within each optical connector.

As illustrated, the diagnostic module 200 may be configured to inspect and/or clean only a subset of the optical connectors. For example, the diagnostic module 200 may be incapable of accessing optical connector 302. Consequently, In additional examples, more than one diagnostic module (not illustrated) may be inserted into the rack. Multiple diagnostic modules may enable faster analysis of the rack system. In addition, the use of multiple diagnostic modules may enable additional features, such as verification of the optical fibers, as will be discussed in more detail herein.

In one example, such as illustrated in FIG. 1, multiple diagnostic modules are inserted into a rack system. The multiple diagnostic modules may include inspection devices, cleaning devices, and additionally a verification device. The verification device is controlled by the controller to transit a predefined optical signal to the optical fiber within the optical connector. A diagnostic module coupled to the verification device via the optical fiber may receive the predefined optical signal and may make a determination on the quality or the received signal. In this manner, both end-faces of an optical fiber may be inspected, cleaned (i.e., by two independent diagnostic modules), and the optical fiber itself may be verified by transmitting and receiving signals between the diagnostic modules.

A verification device, similar to the inspection device and the cleaning device, may include a low resolution camera. The low resolution camera may be controlled by the controller and utilized to guide the verification device into an appropriate position. The verification device may comprise a blind-mate optical connector configured to mate with the optical connector disposed on the backplane. Once mated with the optical connector on the backplane, the verification device may send a predefined optical signal to an optical receiver in another diagnostic module. The receiving diagnostic module may then verify the received signal for correctness and signal quality. A diagnostic module may communicate with one or multiple other diagnostic modules for the verification process.

Figure 4:
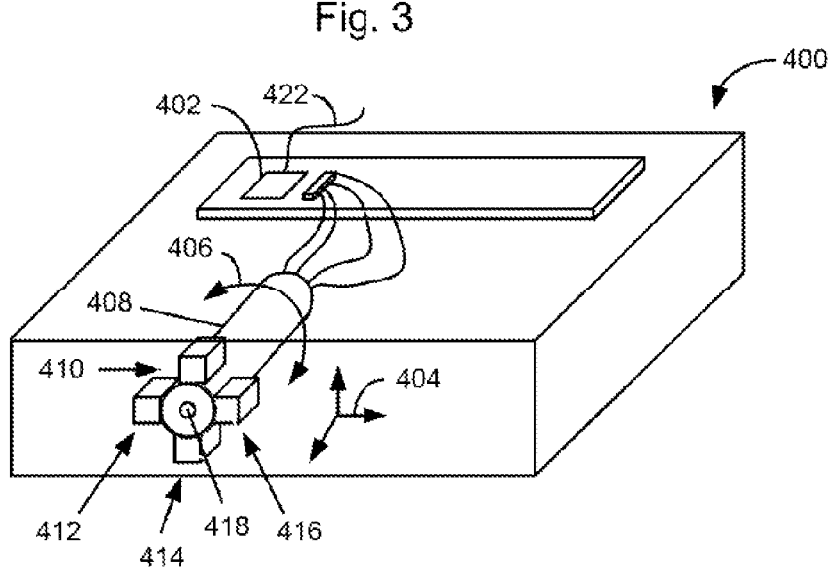
FIG. 4 is a perspective view of another diagnostic module according to some implementations.

Referring to FIG. 4, another example of a diagnostic module is illustrated. The diagnostic module 400 includes an inspection device 410, a cleaning device 412, and two verification devices 414, 416. The various devices are coupled to one another and configured to rotate about the circular direction 406 to provide a respective device to an optical connector. The various devices are coupled to a controller 402 which may actuate the devices to retract, extend, transition (vertical and horizontal) between various connectors as indicated by arrows 404, and rotate 406 to present one of the devices to the optical connector.

To locate the optical connector or cleaning, inspection, and verification, a shared camera 418 may be utilized by the controller. Based on images received from camera 418, the controller 402 may control an actuation mechanism to correctly position the combined system 408, to rotate the system 408 into a determined orientation and to engage the respective device. In this manner, the device may first inspect an end-face of an optical fiber, rotate to a cleaning device while remaining in the correct location, clean the optical fiber end-face, rotate again to select the appropriate connector, and then verify the optical fiber. Other sequences are contemplated. This implementation may negate the need for multiple rails and actuation mechanisms. The controller 402 may communicate with an external manager via the external link 422, to receive instructions and to report the results. Link 422 may be either a wired link or a wireless link.

Figures 5, 6:
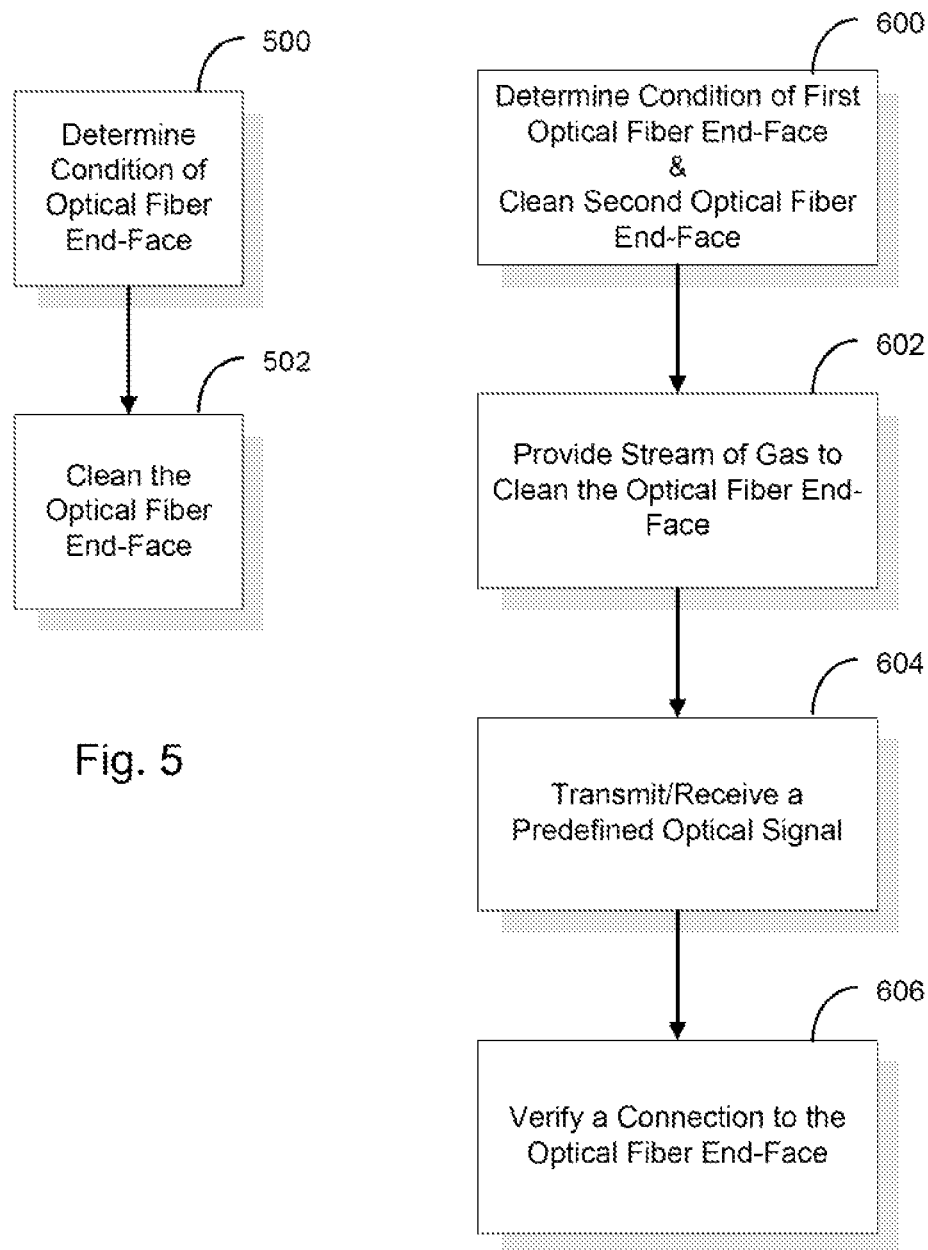
FIGS. 5-6 are flow diagrams according to some implementations.

FIGS. 5-6 are flow diagrams according to some implementations. The processes of FIG. 5-6 are merely for illustrative purposes, and are not meant to imply various functions are order dependent. Other processes are contemplated.

The process of FIG. 5 provides (at 500) determining a condition of a first optical fiber end-face within an optical connector via actuation of an inspection device from a first position to a second position. Upon determination of the condition, the process provides (at 502) cleaning the first optical fiber end-face within the optical connector via actuation of a cleaning device from a first position to a second position. In one example, the first position is a retracted position and the second position is an extended position, for both the inspection device and the cleaning device. In various examples, cleaning the first optical fiber end-face may comprise utilizing a material having a cleaning solution disposed thereon, or alternatively, utilizing a blast of compressed gas to dislodge debris and/or dust. Other cleaning solutions are contemplated.

Similar to the process of FIG. 5, FIG. 6 provides (at 600) determining a condition of a first optical fiber end face within an optical connector via actuation of an inspection device from a first position to a second position. In addition, the diagnostic module may simultaneously clean a second optical fiber end-face within a second optical connector via actuation of a cleaning device from a first position to a second position. In various examples, the first position may be a retracted position and the second position may be an extended position.

Upon the parallel inspection and cleaning of the first and second optical fiber end-faces, the process may provide (at 602) providing a stream of gas to clean the first optical fiber end-face of the optical connector. For example, upon cleaning of the second optical fiber end-face, a control may actuate the cleaning device to transition to the first optical connector to perform a cleaning subsequent to the inspecting device having determined the condition of the first optical fiber end-face.

Upon the cleaning of various optical fiber-end faces, a diagnostic module configured with a verification device may transmit and receive a predefined optical signal across the optical fiber. The predefined optical signal may be known at both ends of the optical media and utilized to characterize the transmission capabilities of the optical fiber, and/or verify a connection of the optical fiber end-face. In various examples, the diagnostic module may iteratively move through multiple optical connectors, inspecting, cleaning, and verifying the optical fiber end-faces and transmission capabilities.

A diagnostic module may communicate with one or multiple other diagnostic modules for the inspection and the verification steps, synchronized by the external manager via the external link (e.g., Ethernet) using a predefined messaging protocol.

In the foregoing description, numerous details are set forth to provide an understanding of the subject disclosed herein. However, implementations may be practiced without some or all of these details. Other implementations may include modifications and variations from the details discussed above. It is intended that the appended claims cover such modifications and variations.

What is claimed is:

1. A system, comprising:
    an inspection device to inspect an optical fiber end-face within an optical connector;
    a cleaning device to clean the optical fiber end-face within the optical connector based on a result of the inspection;
    a controller coupled to the inspection device and the cleaning device to selectively locate the optical connector and actuate both the inspection device to inspect the optical fiber end-face and the cleaning device to clean the optical fiber end-face; and
    an actuator coupled to the controller, wherein the actuator is to actuate the inspection device and the cleaning device between a retracted position and an extended position, wherein the inspection device and the cleaning device interface with the optical fiber end-face in the extended position.

2. The system of claim 1, wherein the inspection device and the cleaning device comprise a camera to locate the optical connector, wherein the optical connector includes identification information.

3. The system of claim 1, wherein the actuator comprises a plurality of rails to facilitate positioning of the inspection device and the cleaning device at a second optical connector.

4. The system of claim 1, wherein the cleaning device comprises an air module to provide a burst of air to clean to the optical fiber end-face.

5. The system of claim 1, wherein the controller comprises an external link to communicate with an external manager via a predefined messaging protocol.

6. The system of claim 1, wherein the controller is to actuate the inspection device simultaneously with the cleaning device.

7. A method, comprising:
    determining a condition of a first optical fiber end-face within an optical connector via actuation of an inspection device from a first position to a second position;
    cleaning the first optical fiber end-face within the optical connector via actuation of a cleaning device from a first position to a second position in response to the determination.

8. The method of claim 7, further comprising:
    receiving a predefined optical signal via the first optical fiber end-face within the optical connector;
    determining a signal quality of the received predefined optical signal to verify a connection of the optical fiber.

9. The method of claim 7, further comprising:
    cleaning a second optical fiber end-face within the optical connector via actuation of the cleaning device from the first position to the second position; and
    wherein cleaning the second optical fiber end-face is simultaneous with determining the condition of the first optical fiber end-face.

10. The method of claim 7, wherein cleaning the first optical fiber end-face comprises providing a burst of air to the first optical fiber end-face.

11. The method of claim 7, further comprising:
    determining a location of the first optical fiber end-face within the optical connector via a camera, wherein the camera is to determine the location based on one or more indicia of the connector.

* * * * *